(12) United States Patent
Haider

(10) Patent No.: US 7,060,119 B1
(45) Date of Patent: Jun. 13, 2006

(54) THERAPEUTIC ABRASIVE SPONGE

(75) Inventor: Michael J. Haider, Westminster, MD (US)

(73) Assignee: Footzee, Inc., Westminster, MD (US)

( * ) Notice: Subject to any disclaimer, the term of this patent is extended or adjusted under 35 U.S.C. 154(b) by 0 days.

(21) Appl. No.: 10/884,349

(22) Filed: Jul. 2, 2004

Related U.S. Application Data

(63) Continuation-in-part of application No. 10/249,871, filed on May 14, 2003, now abandoned.

(51) Int. Cl.
*B24D 15/04* (2006.01)

(52) U.S. Cl. .................... 51/298; 451/523; 451/495

(58) Field of Classification Search ............. 451/523, 451/524, 490, 539, 538, 558, 495; 15/160, 15/210.1; 51/298, 296
See application file for complete search history.

(56) References Cited

U.S. PATENT DOCUMENTS

| | | | | |
|---|---|---|---|---|
| 2,112,593 A | * | 3/1938 | Campbell | 451/502 |
| 2,493,852 A | * | 1/1950 | Bonkowski | 451/504 |
| 2,780,533 A | * | 2/1957 | Hurst | 51/297 |
| 3,653,859 A | * | 4/1972 | Zimmer et al. | 451/533 |
| 4,421,526 A | * | 12/1983 | Strickman et al. | 51/296 |
| 4,887,396 A | * | 12/1989 | Lukianoff | 451/523 |
| 5,131,193 A | * | 7/1992 | Demers | 451/524 |
| 6,439,988 B1 | * | 8/2002 | Long et al. | 451/495 |
| 6,685,376 B1 | * | 2/2004 | Weihrauch | 401/196 |

FOREIGN PATENT DOCUMENTS

JP          60-48266       * 3/1985       ............. 451/524

\* cited by examiner

*Primary Examiner*—Robert A. Rose
(74) *Attorney, Agent, or Firm*—William S. Ramsey

(57) ABSTRACT

The foot smoothing pad has a polyurethane foamed core which is coated with particulate abrasive material. The pad is water resistant and completely washable and may be used either wet or dry. It is used to remove buildup of rough, dry skin, especially on the feet and hands. The soft and resilient texture of the pad insures comfort and ease in smoothing the skin. The large inside curved surfaces are used to smooth the heels, and the rounded sides may be used for smaller areas, such as the toes.

3 Claims, 5 Drawing Sheets

THERAPEUTIC ABRASIVE SPONGE

CROSS-REFERENCE TO RELATED APPLICATIONS

This application is a continuation-in-part of U.S. utility patent application Ser. No. 10/249,871, filed May 14, 2003, herewith abandoned.

STATEMENT REGARDING FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Field of the Invention

This invention pertains to abrasive pads used for the purpose of maintaining and supporting foot health.

2. Description of Related Art Including Information Disclosed Under 37 CFR 1.97 and 37 CFR 1.98

The foot smoothing pad of the present invention provides a water-resistant completely washable pad for removing rough, dry skin from the feet and other body areas, such as the hands, thereby restoring the skin's natural softness. The pad is soft and contoured for ease in handling and is applicable to treatment of large areas, such as the heels, and small areas, such as the toes.

U.S. Pat. No. 3,857,133 discloses a polyurethane sponge with a sponge-like body and a surface layer of abrasive open cell polyurethane. The sponge is comprised of a closed cell core foam and an open cell surface foam. The abrasive effect is obtained from the structure of the open cell polyurethane on the surface of the sponge. The sponge is used for a combination of scrubbing and wiping.

U.S. Pat. No. 4,344,930 discloses an open celled polyurethane sponge containing a skin care composition dispersed into the sponge. The skin care composition is dispersed on the skin when the sponge is used.

U.S. Pat. No. 4,627,129 discloses a polyurethane sponge for body cleaning with a specific shape of a flat scrubbing surface and a cup-shaped hand holding back with provisions for a finger insertion. The material is characterized as mildly abrasive.

U.S. Pat. No. 4,966,609 discloses an abrasive sponge made of preferably polyvinyl chloride, but polyurethane also is disclosed, with abrasive materials attached by adhesives, or by binders such as rubber. This sponge is comprised of a flexible foam substrate with a reinforcing textile layer.

U.S. Pat. No. 5,640,737 discloses sponges comprised of at least two layers of polyurethane foam with the outer layers softer than the interior and which may be formed in a variety of shapes.

U.S. Pat. No. 6,142,156 discloses a wide variety of shapes of solid abrasive structures which are attached to a bathtub or shower for foot treatment. The structures may be made of pumice, concrete, silica, glass stone, volcanic rock, or sand and styrofoam and a pumice sponge made of pumice and polyethylene.

U.S. Pat. No. 6,491,928 discloses cleansing articles in both concave and convex shapes which include a wide variety of cleansing compounds.

None of the discovered prior art discloses articles with the structure and advantages of the present invention, that is, a water-resistant abrasive pad which may be used dry or wet and which is shaped for efficient and optimum use on the feet and hands.

BRIEF SUMMARY OF THE EMBODIMENTS OF THE INVENTION

Disclosed in this patent application are embodiments of a therapeutic abrasive sponge comprised of open celled sponge material having a front and a back panel, a top and a bottom panel, and a left end and a right end panel. The front panel having a concave shape, the top panel and bottom panel having a flat shape and a width, the left end panel and right end panel having a hemispheric shape with a radius. Particulate material is adhered to at least one panel.

The process of manufacture of embodiments of a therapeutic abrasive sponge comprises several steps. Step one is obtaining a suitably-shaped piece of foamed sponge material. In step two particulate abrasive material is mixed with adhesive. The foamed sponge material is coated with particulate abrasive material mixed with adhesive in step three. The coating is done by spraying the foamed sponge material with the particulate abrasive material, or dipping the foamed sponge material into the particulate abrasive material in step four. Step five involves curing the foamed sponge material coated with particulate abrasive material.

The objective of the embodiments of this invention is to provide an abrasive sponge for removing rough and injured skin from hands and feet.

Another objective of the embodiments of this invention is to provide an abrasive sponge which is water resistant.

Another objective of the embodiments of this invention is to provide a soft abrasive sponge which removes rough, dry, scaly and cracked skin.

Another objective of the embodiments of this invention is to provide an abrasive sponge which is soft and contoured for comfort and ease of use.

Another objective of the embodiments of this invention is to provide an abrasive sponge which is completely washable.

Another objective of the embodiments of this invention is to provide an abrasive sponge which restores skin on the feet, elbows, and hands to natural softness.

Another objective of the embodiments of this invention is to provide an abrasive sponge shaped to facilitate treatment of the heels and other body surfaces.

A final objective of the embodiments of this invention is to provide an abrasive sponge which is easily and inexpensively manufactured without adverse effects on the environment.

DETAILED DESCRIPTION OF THE EMBODIMENTS OF THE INVENTION

The sponge is comprises of an open-celled polymer foam such as polyurethane although other open-cell polymers may be used. The nature of the foam material will enable the invention to conform to the area of the body being abraded but will regain its original shape after any deforming pressure has been removed and will also enable the invention to retain its shape after multiple deformations.

The abrasive material adhered directly to the sponge shall be of a waterproof nature and will maintain its consistency and abrasive qualities during any deforming pressure of the sponge and retain the abrasive qualities after multiple deformations of the sponge.

Figure 1:
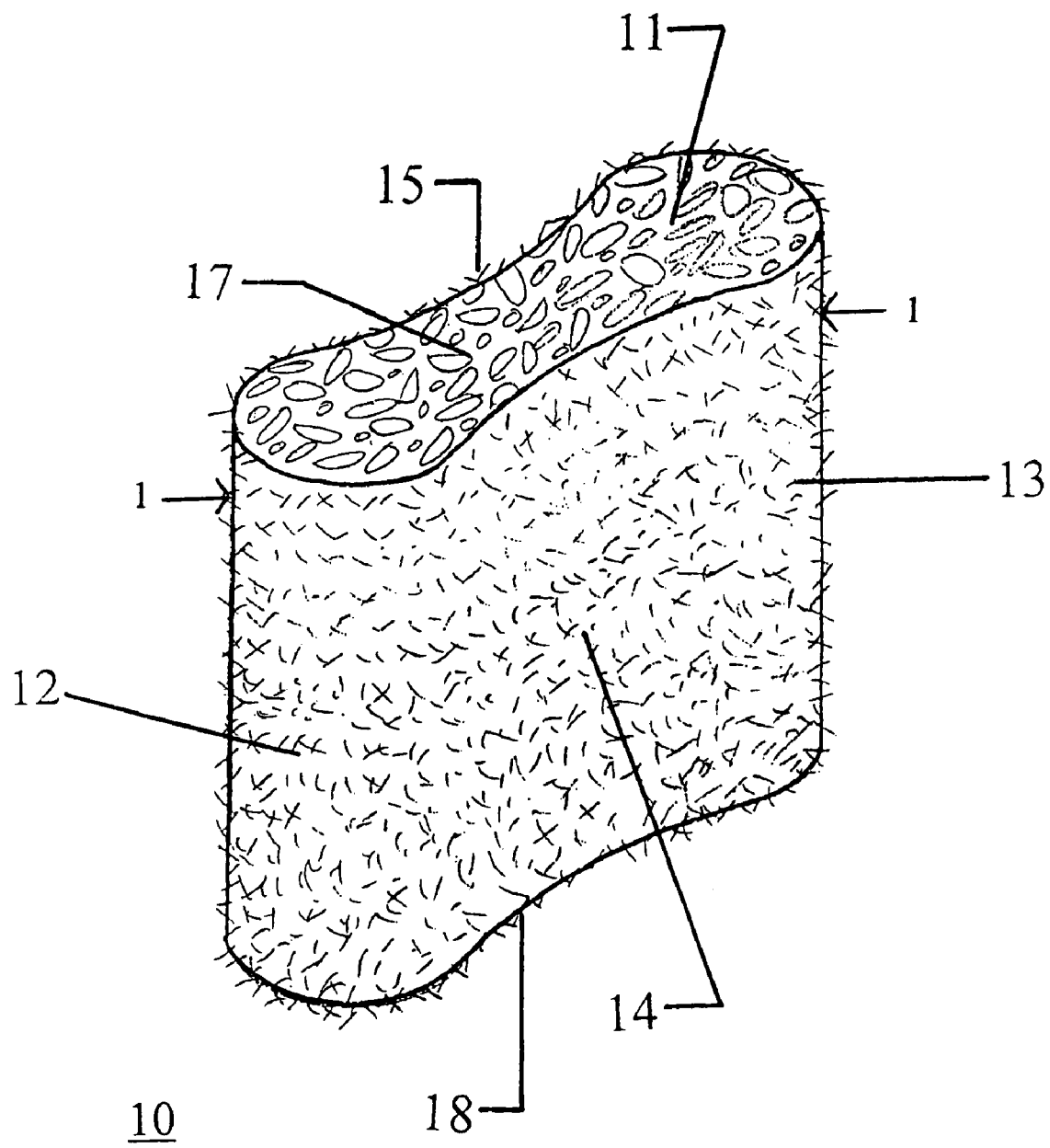
FIG. 1. is a perspective view of the first embodiment therapeutic sponge.

FIG. 1. is a perspective view of the first embodiment therapeutic sponge 10. Visible in FIG. 1 is the open celled sponge material 11 with a front panel 14 and back panel 15 (not fully visible in FIG. 1), a first radiused side 12 having an arcuate shape with a radius in cross section is at one end and a second radiused side 13 is at the other end, a top side 17 is visible and a bottom side 18 (not visible in FIG. 1) is the same as the top side. A coating 16 comprised of a mixture of coating material and particulate abrasive material covers the front panel 14 and back panel 15, the first radiused side 12 and the second radiused side 13 and is visible on the top side 17. In the first embodiment the first radiused side 12 has approximately the same radius as the second radiused side 13. In the first embodiment the front panel 14 and back panel 15 are concave in cross section.

Figure 2:
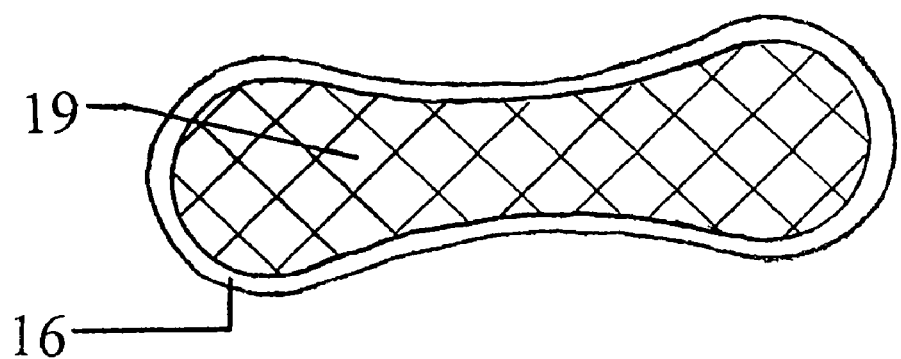
FIG. 2 is a cross section view of the first embodiment therapeutic sponge taken at arrows 1—1 in FIG. 1.

FIG. 2 is a cross section view of the first embodiment therapeutic sponge taken at arrows 1—1 in FIG. 1. Visible in FIG. 2 is the open-cell polymer material 19 which comprises the base of the therapeutic sponge. The coating 16 covers the front 14, and back 15 panels and the first 12 and second 13 radiused sides. Coating 16 is comprised of coating material and particulate abrasive material.

The first embodiment therapeutic abrasive sponge is shaped to enable comfortable and secure gripping in the hand of the user. The concave front and back panels are shaped for use on surfaces such as the heel and ankle regions.

Figure 3:
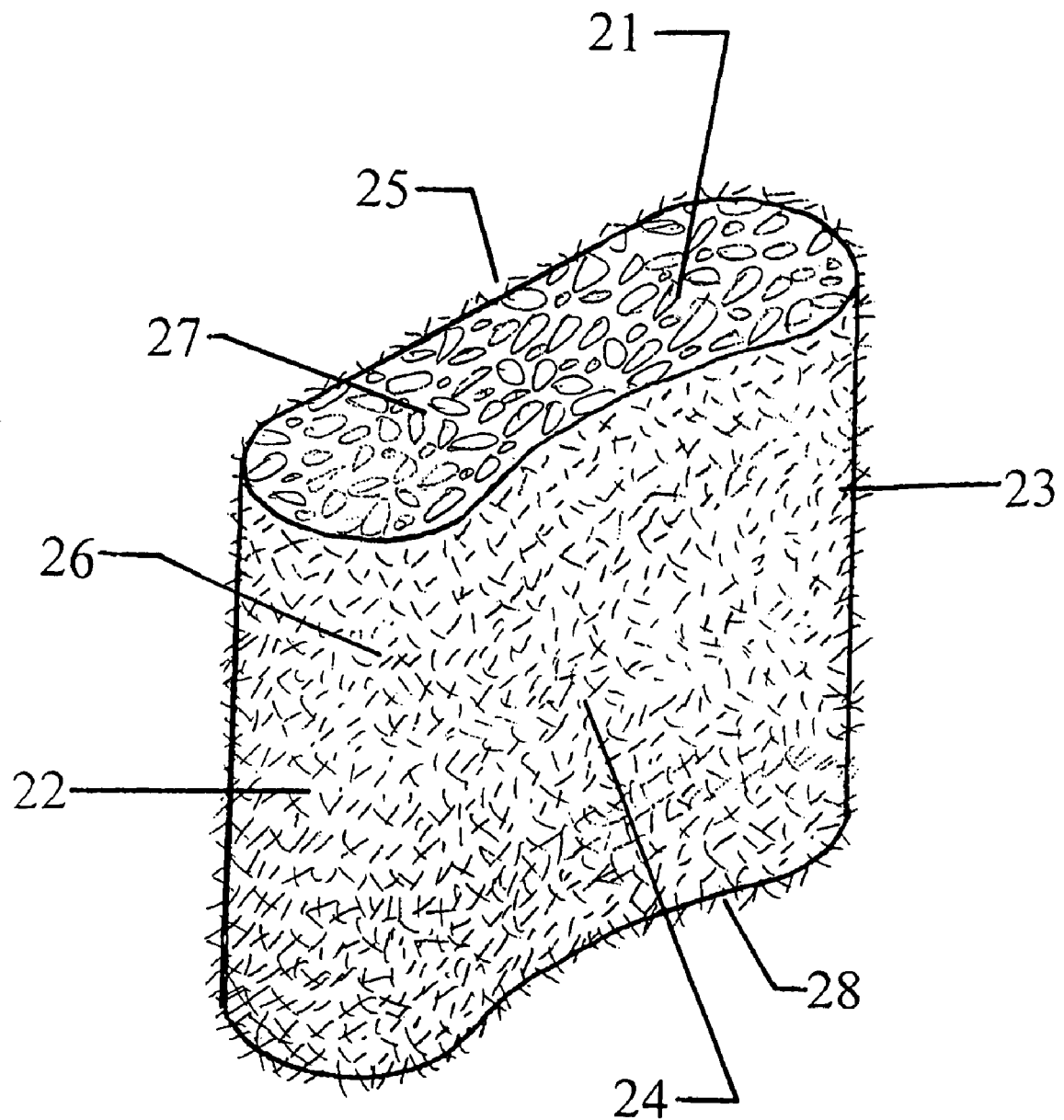
FIG. 3 is a perspective view of a second embodiment therapeutic sponge.

FIG. 3. is a perspective view of the second embodiment therapeutic sponge 20. Visible in FIG. 3 is the open celled sponge material 21 with a front panel 24 and back panel 25 (not fully visible in FIG. 3), a first radiused side 22 having an arcuate shape with a radius in cross section is at one end and a second radiused side 23 is at the other end, a top side 27 is visible and a bottom side 28 (not visible in FIG. 3) is the same as the top side. A coating 26 comprised of a mixture of coating material and particulate abrasive material covers the front panel 24 and back panel 25, the first radiused side 22 and the second radiused side 23 and is visible on the top side 27. In the second embodiment the first radiused side 22 has approximately the same radius as the second radiused side 23. In the second embodiment the front panel 24 is concave in cross section and the back panel 25 is flat in cross section.

The second embodiment therapeutic abrasive sponge is shaped to enable comfortable and secure gripping in the hand of the user. The concave front panel is shaped for use on curved surfaces such as the heel and the back panel is flat for use on large relatively flat body surfaces such as the back.

Figure 4:
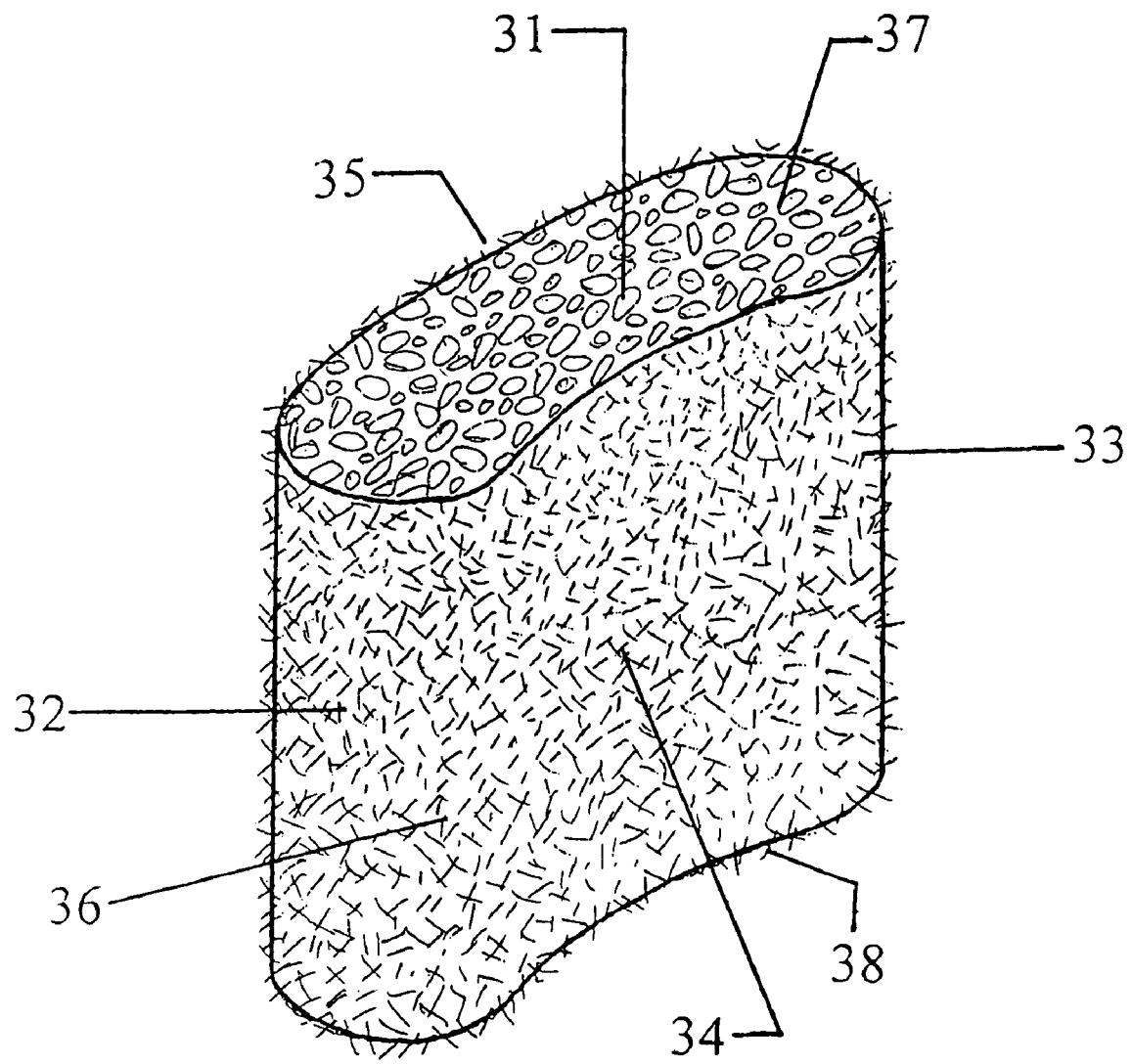
FIG. 4. is a perspective view of a third embodiment therapeutic sponge.

FIG. 4. is a perspective view of a third embodiment therapeutic sponge 30. The third embodiment therapeutic abrasive sponge is shaped to enable comfortable and secure gripping in the hand of the user. Visible in FIG. 4 is the open celled sponge material 31 with a front panel 34 and back panel 35 (not fully visible in FIG. 4), a first radiused side 32 having an arcuate shape with a radius in cross section is at one end and a second radiused side 33 is at the other end, a top side 37 is visible and a bottom side 38 (not visible in FIG. 4) is the same as the top side. A coating 36 comprised of a mixture of coating material and particulate abrasive material covers the front panel 34 and back panel 35, the first radiused side 32 and the second radiused side 33 and is visible on the top side 37. In the third embodiment the first radiused side 32 has approximately the same radius as the second radiused side 33. In the third embodiment the front panel 34 is concave in cross section and the back panel 35 is convex in cross section.

The third embodiment therapeutic abrasive sponge is shaped to enable comfortable and secure gripping in the hand of the user. The concave front panel is shaped for use on curved surfaces such as the heel and the back panel is convex for use on inwardly curved or concave body surfaces such as the back of the knee.

Figure 5:
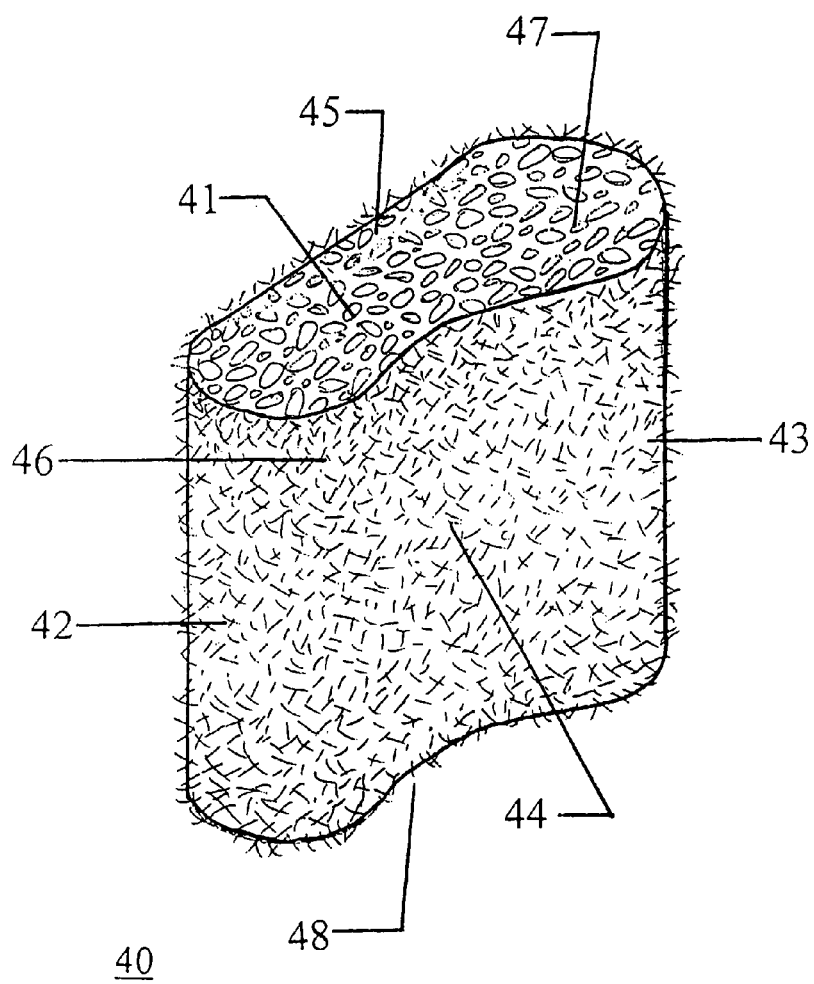
FIG. 5 is a perspective view of a fourth embodiment therapeutic sponge.

FIG. 5. is a perspective view of a fourth embodiment therapeutic sponge 40. The fourth embodiment therapeutic abrasive sponge is shaped to enable comfortable and secure gripping in the hand of the user. Visible in FIG. 5 is the open celled sponge material 41 with a front panel 44 and back panel 45 (not fully visible in FIG. 5), a first radiused side 42 having an arcuate shape with a radius in cross section is at one end and a second radiused side 43 is at the other end, a top side 47 is visible and a bottom side 48 (not visible in FIG. 5) is the same as the top side. A coating 46 comprised of a mixture of coating material and particulate abrasive material covers the front panel 44 and back panel 45, the first radiused side 42 and the second radiused side 43 and is visible on the top side 47. In the fourth embodiment the first radiused side 42 has a radius larger than the radius of the second radiused side 43. In the fourth embodiment the front panel 44 is concave in cross section and the back panel 45 is flat in cross section.

The fourth embodiment therapeutic abrasive sponge is shaped to enable comfortable and secure gripping in the hand of the user. The first and second radiused sides differ to allow convenient gripping by persons with larger or smaller hands. The concave front panel is shaped for use on curved surfaces such as the heel and the back panel is flat for use on relatively flat body surfaces such as the back.

The distance between the first and second radiused sides may be from approximately 2 to approximately 6 inches. A preferred distance is approximately 3 inches. The distance between the front and back sides may be from approximately ¼ to approximately 1 inch. A preferred distance is approximately ½ inch. The distance between the top and bottom sides may be from approximately 2 to approximately 8 inches. A preferred distance is approximately 4 inches. The radius of the first and second radiused sides may be from approximately ¼ to approximately 1 inch. A preferred radius is approximately ½ inch.

Any strong, flexible, resilient polymeric foam may be used for the foam sponge material. Suitable materials include polyurethane, polyolefin, polyvinyl chloride, polyisocyanurate and latex foams.

Any suitable hard, water resistant, and inexpensive particulate material may be used. Suitable particulate materials silicon dioxide, garnet, emery, cryolite, aluminum oxide, silicon carbide, zirconium oxide, silicon carbide, boron carbide, tin oxide, and cerium oxide. Suitable particulate material has a mesh size of Standard Sieve Series 12 to 240 which correspond to particulate diameter of approximately 0.0661 inch to 0.0024 inch.

Any suitable adhesive, resilient, flexible, inexpensive adhesive coating material may be used to attach the particulate material to the foam and coat the panels and sides of the sponge. Suitable coatings include polyurethane, natural rubber, synthetic rubber, polyester, acrylate resin and olefinic resin.

A preferred embodiment abrasive sponge is comprised of polyurethane foam coated with a mixture of polyurethane coating and aluminum oxide abrasive.

A preferred polyurethane foam is foam type-OH58N (CD162522GA) which may be obtained from Rempac Foam Corporation, Clifton, N.J. Characteristics of the preferred foam follow: IFD 25% @2 inches, 162–198. Density, 5.17–6.32 pounds per cubic foot. Minimum tensile strength, 55 pounds per square inch. Minimum elongation, 75 percent. Minimum tear strength, 3.0 pounds per inch. Polyurethane foam is a reaction product of polyethylene glycol and toluene diisocyanate.

A preferred polyurethane coating is a reaction product of polyethylene glycol and diphenyl methane diisocyanate.

A preferred aluminum oxide abrasive passes a Standard Sieve Series 60.

A preferred method of manufacture is to mold polyurethane foam in a rectangular mold. The rectangular foam slab is then shaped to the final shape with contoured surfaces using shapers and sanders. The shaped foam is then coated with a mixture of polyurethane adhesive and aluminum oxide abrasive. The coated sponge is cured to allow fixture of the aluminum oxide to the polyurethane sponge.

In another process of manufacture of a therapeutic abrasive sponge the sponge is impreganted with particulate abrasive material. In this process, a pre-polymer is formed by reacting a polyoxyalkylene polyol with a stoichiometric excess of an organic polyioscyanate. A particulate abrasive material is mixed with the pre-polymer. The pre-polymer particulate abrasive material mixture is then mixed with 30 to 200 percent by weight of the pre-polymer of water, forming a polyurethane foam sponge material impregnated with abrasive material. The sponge is then cured. The sponge is then cut to a suitable size and shaped into a desirable shape. In this process a preferred polyoxyalkylene polyol is polyoxyethylenated glycerol. In this process a preferred organic polyisocyanate is triphenyl methane-4,4', 4"-triisocyanate.

It will be apparent to those skilled in the art that the examples and embodiments described herein are by way of illustration and not of limitation, and that other examples may be used without departing from the spirit and scope of the present invention, as set forth in the appended claims.

I claim:

1. The process of manufacture of a therapeutic abrasive sponge in which a polyurethane foam sponge is impregnated with particulate abrasive material comprising the steps:
    a. forming a pre-polymer by reacting a polyoxyalkylene polyol with a stoichiometric excess of an organic polyioscyanate,
    b. mixing particulate abrasive material with the pre-polymer,
    c. mixing the pre-polymer particulate abrasive material mixture with 30 to 200 percent by weight of the pre-polymer of water,
    d. curing the polyurethane foam sponge material impregnated with particulate abrasive material, and
    e. shaping the polyurethane foam sponge material impregnated with particulate abrasive material into a suitable shape.

2. The process of claim 1 wherein the polyoxyalkylene polyol is polyoxyethylenated glycerol.

3. The process of claim 1 wherein the organic polyisocyanate is triphenyl methane-4,4', 4"-triisocyanate.

* * * * *